(12) United States Patent
Lee et al.

(10) Patent No.: US 11,052,384 B2
(45) Date of Patent: Jul. 6, 2021

(54) CHROME COMPOUND, CATALYST SYSTEM USING SAME, AND METHOD FOR PREPARING ETHYLENE OLIGOMER

(71) Applicants: AJOU UNIVERSITY INDUSTRY—ACADEMIC COOPERATION FOUNDATION, Suwon-si (KR); S-PRECIOUS CATALYSTS INC., Gyeongju-si (KR)

(72) Inventors: Bun Yeoul Lee, Suwon-si (KR); Eun Ho Kim, Seoul (KR); Hyun Mo Lee, Suwon-si (KR)

(73) Assignees: AJOU UNIVERSITY INDUSTRY-ACADEMIC COOPERATION FOUNDATION, Suwon-si (KR); S-PRECIOUS CATALYSTS INC., Gyeongju-si (KR)

( * ) Notice: Subject to any disclaimer, the term of this patent is extended or adjusted under 35 U.S.C. 154(b) by 120 days.

(21) Appl. No.: 16/346,735

(22) PCT Filed: Dec. 12, 2016

(86) PCT No.: PCT/KR2016/014517
§ 371 (c)(1),
(2) Date: May 1, 2019

(87) PCT Pub. No.: WO2018/084365
PCT Pub. Date: May 11, 2018

(65) Prior Publication Data
US 2019/0308179 A1 Oct. 10, 2019

(30) Foreign Application Priority Data

Nov. 2, 2016 (KR) .......................... 10-2016-0145418
Dec. 7, 2016 (KR) .......................... 10-2016-0165965

(51) Int. Cl.
*C08F 4/06* (2006.01)
*B01J 31/14* (2006.01)
(Continued)

(52) U.S. Cl.
CPC ............. *B01J 31/189* (2013.01); *B01J 31/14* (2013.01); *B01J 31/16* (2013.01); *C07C 2/30* (2013.01);
(Continued)

(58) Field of Classification Search
None
See application file for complete search history.

(56) References Cited

U.S. PATENT DOCUMENTS

| 6,511,936 B1 | 1/2003 | Theopold et al. |
| 2005/0187098 A1 | 8/2005 | Knudsen et al. |

(Continued)

FOREIGN PATENT DOCUMENTS

| EP | 1716089 | 11/2006 |
| JP | 2002503733 A | 2/2002 |

(Continued)

OTHER PUBLICATIONS

Ronellenfitsch, M. et al., "Chromium Aryl Complexes with N-Donor Ligands as Catalyst Precursors for Selective Ethylene Trimerization", Organometallics, 2014, vol. 33, No. 22, pp. 5758-5766 (14 pages total).

(Continued)

*Primary Examiner* — Yun Qian
(74) *Attorney, Agent, or Firm* — Sughrue Mion, PLLC (57) ABSTRACT

The present invention relates to a chrome compound composed of non-coordinating anions and a trivalent chrome cation, a reactant of the chrome compound and a bidentate ligand, an ethylene oligomerization reaction catalyst system using the chrome compound and the reactant, and a method (Continued)

for preparing an ethylene oligomer using the catalyst system. Through the above conformation, the present invention can selectively produce 1-hexene and 1-octene with high activity while omitting the use of methylaluminoxane (MAO), and can provide an ethylene oligomerization process more suitable for mass production.

11 Claims, 1 Drawing Sheet

(51) Int. Cl.
    *C07F 11/00* (2006.01)
    *B01J 31/18* (2006.01)
    *C07C 2/32* (2006.01)
    *B01J 31/16* (2006.01)
    *C07F 19/00* (2006.01)
    *C07C 2/30* (2006.01)
    *C07C 11/04* (2006.01)

(52) U.S. Cl.
    CPC ............... *C07C 2/32* (2013.01); *C07F 19/00* (2013.01); *B01J 2231/20* (2013.01); *B01J 2531/62* (2013.01); *C07C 11/04* (2013.01); *C07C 2521/02* (2013.01); *C07C 2523/26* (2013.01); *Y02P 20/52* (2015.11)

(56) References Cited

U.S. PATENT DOCUMENTS

| | | |
|---|---|---|
| 2007/0185362 A1 | 8/2007 | Lattner et al. |
| 2008/0221285 A1* | 9/2008 | Walter ................ B01J 31/1805 526/120 |
| 2012/0316303 A1† | 12/2012 | Hanton |
| 2017/0267603 A1 | 9/2017 | Im et al. |

FOREIGN PATENT DOCUMENTS

| | | |
|---|---|---|
| JP | 2008533030 A | 8/2008 |
| WO | 2005082816 A1 | 9/2005 |
| WO | 2008085653 A1 | 7/2008 |
| WO | 2016129901 A1 | 8/2016 |

OTHER PUBLICATIONS

Lucciulli, S. et al., "Towards Selective Ethylene Tetramerization", Angewandte Chemie, International Edition, 2010, vol. 49, No. 48, pp. 9225-9228 (4 pages total).

European Patent Office: Communication dated Feb. 12, 2020 from in application No. 16920630.7.

Stennett et al., Avoiding Mao: Alternative Activation Methods in Selective Ethylene Oligomerization, 6960-6965, Sep. 20, 2012, American Chemical Society, Organometallics, https://pubs.acs.org/journal/orgnd7.†

\* cited by examiner
† cited by third party

CHROME COMPOUND, CATALYST SYSTEM USING SAME, AND METHOD FOR PREPARING ETHYLENE OLIGOMER

CROSS REFERENCE TO RELATED APPLICATIONS

This application is a National Stage of International Application No. PCT/KR2016/014517 filed Dec. 12, 2016, claiming priority based on Korean Patent Application No. 10-2016-0145418, filed Nov. 2, 2016 and Korean Patent Application No. 10-2016-0165965 filed Dec. 7, 2016.

TECHNICAL FIELD

The present invention relates to a chromium compound, a catalyst system using the same, and a method of preparing an ethylene oligomer, and more particularly, to a cationic chromium compound capable of preparing 1-hexene and 1-octene through the selective oligomerization reaction of ethylene, a catalyst system using the same, and a method of preparing an ethylene oligomer.

BACKGROUND ART 1-hexene and 1-octene, which are ethylene oligomers, are, for example, compounds used in a large amount as co-monomers for the polymerization of a polyolefin such as polyethylene. In particular, as the production of polyolefins using a homogeneous metallocene-based catalyst has recently increased, demand for 1-hexene and 1-octene continues to increase.

According to the related art, various 1-alkenes having about 4 to about 30 carbon atoms are produced by oligomerizing ethylene in a Shell higher olefin process (SHOP) based on a nickel catalyst and are separated, thereby obtaining 1-hexene and 1-octene, but thereafter, a catalyst system capable of selectively producing only 1-hexene or 1-hexene and 1-octene by selectively oligomerizing ethylene was developed.

As an example, a catalyst system developed by Phillips selectively produces only 1-hexene by trimerizing ethylene and began to be commercially available in the early 2000s (Patent Document 1).

As another example, a catalyst system developed by Sassol consists of a chromium trivalent compound ($CrCl_3$ or $Cr(acac)_3$), $isoPrN(PPh_2)_2$, which is a bisphosphine ligand, and methylaluminoxane (MAO) and selectively produces 1-octene and 1-hexene (Patent Document 2, Non-Patent Document 1).

However, the catalyst system developed by Sassol has a drawback in that catalyst performance is realized only when an excess amount of expensive methylaluminoxane (MAO) is used, and thus there is an obstacle to commercialization thereof. That is, the catalyst system developed by Sassol exhibits high activity only when an excess amount of MAO is added such that a molar ratio of Al/Cr ranges from about 300 to about 500, and MAO, which is a compound obtained by reacting expensive trimethylaluminum with water, has a very high production cost compared to other alkylaluminums widely used in industry.

For this reason, efforts have recently been made to develop a catalyst system not using MAO. However, it is very difficult to realize sufficiently high activity without using MAO with only a conventional technique, and it is more difficult to mass-produce a compound or catalyst system exhibiting high activity.

CITED REFERENCES

Patent Document 1: U.S. Pat. No. 5,376,612
Patent Document 2: Korean Patent Publication No. 10-2006-0002742
Patent Document 3: U.S. Pat. No. 7,511,183
Non-Patent Document 1: Journal of the American Chemical Society, 126 (2004) 14712
Non-Patent Document 2: New Journal of Chemistry, 29 (2005) 366
Non-Patent Document 3: Chem. Eur. J. 2001, 7, 490
Non-Patent Document 4: Journal of Organometallic Chemistry, 135 (1977) C6-C9
Non-Patent Document 5: Inorganic Chemistry 2013, 52, 40264039
Non-Patent Document 6: J. AM. CHEM. SOC. 2004, 126, 14712-1471
Non-Patent Document 7: Organometallics 2007, 26, 1108

DISCLOSURE

Technical Problem

An object of the present invention is to provide a chromium compound capable of selectively preparing 1-hexene and 1-octene with high activity without using methylaluminoxane (MAO), and a catalyst system using the chromium compound.

Another object of the present invention is to provide a method of preparing an ethylene oligomer, whereby 1-hexene and 1-octene are selectively prepared with high activity without using methylaluminoxane (MAO), through the chromium compound and the catalyst system using the chromium compound.

The aforementioned and other objects of the present invention will become apparent from the following description.

Technical Solution

According to an embodiment of the present invention, there is provided a chromium compound represented by Formula 1 below:

[Formula 1]

wherein, in Formula 1, X is each independently a halogen, a $C_2$-$C_{30}$ carboxylate, acetylacetonate, or a $C_1$-$C_{30}$ hydrocarbyl having or not having at least one of an ether group and an amine group; L is each independently a $C_2$-$C_{30}$ nitrile, a $C_2$-$C_{30}$ ether, or a $H_2O$ ligand; n is an integer of 0 to 4; A is boron; and Y is a $C_6$-$C_{20}$ fluorine-substituted aryl, a $C_6$-$C_{20}$ fluorine-substituted aryloxy, or a $C_1$-$C_{20}$ fluorine-substituted alkoxy.

In Formula 1, X may be chlorine, and $[AY_4]^-$ may be $[B(C_6F_5)_4]^-$ or $[B((3,5-(CF_3)_2C_6H_3)_4]^-$.

In Formula 1, X may be ortho-(N,N-dimethylamino) benzyl, and $[AY_4]^-$ may be $[B(C_6F_5)_4]^-$ or $[B((3,5-(CF_3)_2C_6H_3)_4]^-$.

According to another embodiment of the present invention, there is provided a chromium compound represented by Formula 2 below:

[Formula 2]

wherein, in Formula 2, (L∩L) is a bidentate chelating ligand; X is each independently a halogen, a $C_2$-$C_{30}$ carboxylate, acetylacetonate, or a $C_1$-$C_{30}$ hydrocarbyl having or not having at least one of an ether group and an amine group; L is each independently a $C_2$-$C_{30}$ nitrile, a $C_2$-$C_{30}$ ether, or a $H_2O$ ligand; m is an integer of 0 to 2; A is boron; and Y is a $C_6$-$C_{20}$ fluorine-substituted aryl, a $C_6$-$C_{20}$ fluorine-substituted aryloxy, or a $C_1$-$C_{20}$ fluorine-substituted alkoxy. The bidentate chelating ligand may be a compound represented by Formula 3 below:

$(R^1)_2P\text{—}Z\text{—}P(R^1)_2$         [Formula 3]

wherein, in Formula 3, $R^1$ is each independently a $C_1$-$C_{50}$ alkyl group or a $C_6$-$C_{50}$ aryl group; Z is a $C_2$-$C_{50}$ alkylene group, a $C_6$-$C_{50}$ arylene group, or —N($R^2$)— that links the two phosphorus (P) atoms to each other; and $R^2$ is a $C_1$-$C_{50}$ alkyl or a $C_6$-$C_{50}$ aryl.

In Formula 3, $R^1$ may be phenyl; and Z may be —N($R^2$)— wherein $R^2$ is a $C_1$-$C_{50}$ alkyl or a $C_6$-$C_{50}$ aryl.

According to another embodiment of the present invention, there is provided an ethylene oligomerization catalyst system including: the chromium compound represented by Formula 2; and an organic aluminum compound represented by Formula 4 below:

$(R^3)_3Al$         [Formula 4]

wherein, in Formula 4, $R^3$ is a $C_1$-$C_{20}$ alkyl group.

In Formula 4, $R^3$ may be ethyl or isobutyl.

In the catalyst system, a molar ratio (Cr:Al) of the chromium compound represented by Formula 2 and the aluminum compound represented by Formula 4 may range from 1:50 to 1:500.

According to another embodiment of the present invention, there is provided a method of preparing an ethylene oligomer, including bringing the catalyst system into contact with ethylene monomers to selectively prepare 1-hexene and 1-octene.

Advantageous Effects

The present invention can provide a cationic chromium compound capable of selectively preparing 1-hexene and 1-octene with high activity without using methylaluminoxane (MAO), and can provide a catalyst system and a method of preparing an ethylene oligomer, which are capable of preparing 1-hexene and 1-octene by using the chromium compound as a catalyst precursor, using a trialkylaluminum or tetraalkylaluminoxane, which is inexpensive, instead of using MAO, which is expensive, and implementing a selective ethylene oligomerization catalytic reaction with high activity.

BEST MODE

Hereinafter, unless otherwise indicated herein, Me denotes methyl, Et denotes ethyl, Pr denotes propyl, iBu denotes isobutyl, Ph denotes phenyl, PE denotes polyethylene, acac denotes acetylacetonate, and THF denotes tetrahydrofuran.

A chromium compound according to an embodiment of the present invention is a novel chromium trivalent compound consisting of a non-coordinating anion and a chromium trivalent cation and is represented by Formula 1 below:

$[X_2CrL_n]^+[AY_4]^-$         [Formula 1]

wherein, in Formula 1, X is each independently a halogen, a $C_2$-$C_{30}$ carboxylate, acetylacetonate (ACAC), or a $C_1$-$C_{30}$ hydrocarbyl having or not having at least one of an ether group and an amine group; L is each independently a $C_2$-$C_{30}$ nitrile, a $C_2$-$C_{30}$ ether, or a $H_2O$ ligand; n is an integer of 0 to 4; A is boron; and Y is a $C_6$-$C_{20}$ fluorine-substituted aryl, a $C_6$-$C_{20}$ fluorine-substituted aryloxy, or a $C_1$-$C_{20}$ fluorine-substituted alkoxy.

The chromium compound according to an embodiment of the present invention may be applied to an ethylene oligomerization reaction to thereby selectively prepare 1-hexene and 1-octene with high activity without using expensive methylaluminoxane (MAO).

In particular, in Formula 1, X may be a halogen, more particularly, fluorine (F), chlorine (Cl), bromine (Br), iodine (I), for example, Cl. In this case, mass productivity of the chromium compound of Formula 1 is further enhanced, and raw materials are readily available.

Alternatively, in particular, in Formula 1, X may be a $C_1$-$C_{30}$ hydrocarbyl having at least one of an ether group or an amine group, more particularly, a $C_1$-$C_{30}$ alkyl group having at least one of an ether group and an amine group, a $C_6$-$C_{30}$ aryl group, or a $C_5$-$C_{30}$ benzyl derivative, for example, ortho-(N,N-dimethylamino)benzyl. In this case, mass productivity of the chromium compound of Formula 1 is further enhanced, and raw materials are readily available.

In particular, in Formula 1, Y may be $C_6F_5$, 3,5-$(CF_3)_2$$C_6H_3$, or $OC(CF_3)_3$, and for example, $[AY_4]^-$ may be $[B(C_6F_5)_4]^-$ or $[B((3,5-(CF_3)_2C_6H_3)_4]^-$. In this case, mass productivity of the chromium compound of Formula 1 is further enhanced, and raw materials are readily available.

In particular, in Formula 1, L, which is a neutral coordinating ligand, may be a $C_2$-$C_{30}$ nitrile, a $C_2$-$C_{30}$ cyclic or acyclic ether, $H_2O$, or a mixture thereof, and more particularly, may be acetonitrile, tetrahydrofuran (THF), diethylether, $H_2O$, or a mixture thereof, for example, acetonitrile or THF. In Formula 1, n may be particularly 2 to 4, for example, 2, 3, or 4, and may vary depending on a vacuum drying degree during preparation. In this case, mass productivity of the chromium compound of Formula 1 is further enhanced, and raw materials are readily available.

In one embodiment, the compound of Formula 1 may be a chromium compound of Formula 1 wherein X is chlorine, $[AY_4]^-$ is $[B(C_6F_5)_4]^-$, L is THF, and n is 4. In this case, mass productivity of the chromium compound of Formula 1 may be further enhanced, raw materials are readily available, and the activity of an ethylene oligomer reaction may be further enhanced.

In another embodiment, the compound of Formula 1 may be, for example, $[Cl_2CrL_n]^+[B(C_6F_5)_4]^-$, $[Cl_2CrL_n]^+[B((3,5-(CF_3)_2C_6H_3)_4]^-$, or the like, but the present invention is not limited thereto. In this case, mass productivity of the chromium compound of Formula 1 may be further enhanced, raw materials are readily available, and the activity of an ethylene oligomer reaction may be further enhanced.

In another embodiment, the compound of Formula 1 may be, for example, [(ortho-Me$_2$NC$_6$H$_4$CH$_2$)$_2$CrL$_n$]$^+$[B(C$_6$F$_5$)$_4$]$^-$, [(ortho-Me$_2$NC$_6$H$_4$CH$_2$)$_2$CrL$_n$]$^+$[B((3,5-(CF$_3$)$_2$C$_6$H$_3$)$_4$]$^-$, or the like. In this case, L, which is a neutral coordinating ligand, may be acetonitrile, THF, diethylether, H$_2$O, or a mixture thereof, and n may range from 0 to 2 and vary depending on a vacuum drying degree during preparation.

In particular, the chromium compound of Formula 1 may be prepared by the reaction of CrX$_3$(L)$_3$ and Ag$^+$[AY$_4$]$^-$ in an acetonitrile solvent. X, L, A, and Y are the same as described above. In this case, not only raw materials may be readily available, but manufacturing costs may also be reduced, and thus this compound is more suitable for use in mass-production processes.

In one embodiment, a chromium compound of Formula 1 wherein X is chlorine, [AY$_4$]$^-$ is [B(C$_6$F$_5$)$_4$]$^-$, L is acetonitrile, and n is 4 may be prepared by the reaction of CrCl$_3$(THF)$_3$ and Ag$^+$[B(C$_6$F$_5$)$_4$]$^-$ in an acetonitrile solvent. The resulting chromium compound has a structure of [Cl$_2$Cr(NCCH$_3$)$_n$]$^+$[B(C$_6$F$_5$)$_4$]$^-$. In addition, the n value may vary depending on the drying degree of the produced chromium compound, but a [Cl$_2$Cr(NCCH$_3$)$_4$]$^+$[B(C$_6$F$_5$)$_4$]$^-$ compound having a well-defined structure wherein n=4 may be obtained by appropriately adjusting the drying degree. The CrCl$_3$(THF)$_3$ compound may be commercially available, and Ag$^+$[B(C$_6$F$_5$)$_4$]$^-$ is a compound that is easily synthesizable by a metathesis reaction of K+[B(C$_6$F$_5$)$_4$]$^-$ and AgNO$_3$, which are commercially available (New Journal of Chemistry, 29 (2005) 366). When the chromium compound of Formula 1 is prepared using this method, mass productivity is further enhanced, raw materials are readily available, and a manufacturing cost reducing effect is very significant.

For example, in one embodiment, a compound such as [Ag]$^+$[B((3,5-(CF$_3$)$_2$C$_6$H$_3$)$_4$]$^-$ or the like may also be used instead of Ag$^+$[B(C$_6$F$_5$)$_4$]$^-$. The synthesis of the [Ag]$^+$[B((3,5-(CF$_3$)$_2$C$_6$H$_3$)$_4$]$^-$ compound has been reported in the following document (New Journal of Chemistry, 29 (2005) 366; Chem. Eur. J. 2001, 7, 490), and a [Cl$_2$CrL$_n$]$^+$[B((3,5-(CF$_3$)$_2$C$_6$H$_3$)$_4$]$^-$ compound may be prepared by a metathesis reaction with CrCl$_3$(THF)$_3$ using the same method as the above-described reaction.

Figure 1:
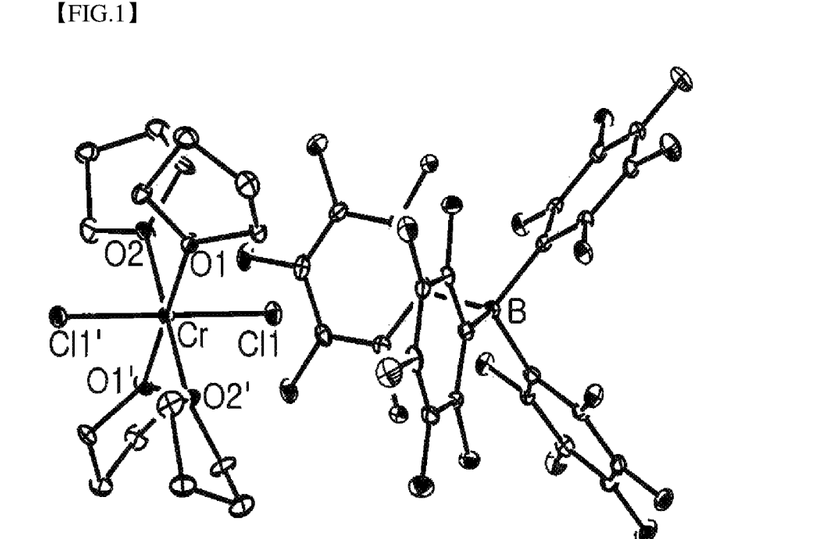
FIG. 1 illustrates a structure of a cationic chromium compound represented by Formula 1B (wherein X is chlorine, L is THF, n is 4, A is boron, and Y is $C_6F_5$) that was prepared according to Example 2, wherein the structure was clearly identified by X-ray crystallography.

In another embodiment, when the prepared [Cl$_2$Cr(NCCH$_3$)$_4$]$^+$[B(C$_6$F$_5$)$_4$]$^-$ compound is dissolved in THF, a [Cl$_2$Cr(THF)$_4$]$^+$[B(C$_6$F$_5$)$_4$]$^-$ compound in which an acetonitrile ligand is substituted with a THF ligand may be prepared. In FIG. 1, the structure of the [Cl$_2$Cr(THF)$_4$]$^+$[B(C$_6$F$_5$)$_4$]$^-$ prepared using the above-described method, which was clearly identified by X-ray crystallography, is illustrated.

In another embodiment, the cationic chromium compound of Formula 1, which is [(ortho-Me$_2$NC$_6$H$_4$CH$_2$)$_2$CrL$_n$]$^+$[B(C$_6$F$_5$)$_4$]$^-$ or [(ortho-Me$_2$NC$_6$H$_4$CH$_2$)$_2$CrL$_n$]$^+$[B((3,5-(CF$_3$)$_2$C$_6$H$_3$)$_4$]$^-$, may be prepared by the reaction of (ortho-Me$_2$NC$_6$H$_4$CH$_2$)$_3$Cr and [H(OEt$_2$)$_2$]$^+$[B(C$_6$F$_5$)$_4$]$^-$ or [H(OEt$_2$)$_2$]$^+$[B((3,5-(CF$_3$)$_2$C$_6$H$_3$)$_4$]$^-$ in a CH$_2$Cl$_2$ solvent. The (ortho-Me$_2$NC$_6$H$_4$CH$_2$)$_3$Cr and [H(OEt$_2$)$_2$]$^+$[B(C$_6$F$_5$)$_4$]$^-$ or [H(OEt$_2$)$_2$]$^+$[B((3,5-(CF$_3$)$_2$C$_6$H$_3$)$_4$]$^-$ may be prepared using a method reported in the following document (Journal of Organometallic Chemistry, 135 (1977) C$_6$-C$_9$; Inorganic Chemistry 2013, 52, 40264039).

A chromium compound according to another embodiment of the present invention is a novel compound represented by Formula 2 below:

$$[(L\cap L)CrX_2L_m]^+[AY_4]^- \quad \text{[Formula 2]}$$

wherein, in Formula 2, (L∩L) is a bidentate chelating ligand; X is each independently a halogen, a C$_2$-C$_{30}$ carboxylate, acetylacetonate, or a C$_1$-C$_{30}$ hydrocarbyl having or not having at least one of an ether group and an amine group; L is each independently a C$_2$-C$_{30}$ nitrile, a C$_2$-C$_{30}$ ether, or a H$_2$O ligand; m is an integer of 0 to 2; A is boron; and Y is a C$_6$-C$_{20}$ fluorine-substituted aryl, a C$_6$-C$_{20}$ fluorine-substituted aryloxy, or a C$_1$-C$_{20}$ fluorine-substituted alkoxy.

In particular, the chromium compound of Formula 2 may be a compound derived from the compound of Formula 1. More particularly, the chromium compound of Formula 2 may be prepared by reacting the compound of Formula 1 and a bidentate chelating ligand (L∩L) of various structures, for example, in a dichloromethane solvent. In this case, the ligand L included in the chromium compound of Formula 1 is substituted with the introduced bidentate chelating ligand (L∩L) such that the chromium compound of Formula 1 is converted to the compound of Formula 2.

In particular, in Formula 2, the bidentate ligand compound may be an organic compound having two atoms capable of coordinating with a metal. Examples of the atoms capable of coordinating with a metal may include phosphorus (P), nitrogen (N), oxygen (O), and the like.

More particularly, in Formula 2, the bidentate ligand compound may be a compound represented by Formula 3 below and containing two P atoms. When having the ligand of Formula 3, the chromium compound of Formula 2 may exhibit much higher activity and high selectivity (selectivity for 1-hexene and 1-octene) when applied to a selective ethylene oligomerization reaction.

$$(R^1)_2P-Z-P(R^1)_2 \quad \text{[Formula 3]}$$

wherein, in Formula 3, R$^1$ is each independently a C$_1$-C$_{50}$ alkyl group or a C$_6$-C$_{50}$ aryl group; and Z is a C$_2$-C$_{50}$ alkylene group, a C$_6$-C$_{50}$ arylene group, or —N(R$^2$)— that links the two P atoms, wherein R$^2$ is a C$_1$-C$_{50}$ alkyl or a C$_6$-C$_{50}$ aryl.

In one embodiment, the chromium compound of Formula 3 may be a compound of Formula 3 wherein R$^1$ is phenyl, and Z is —N(R$^2$)— wherein R$^2$ is a C$_1$-C$_{50}$ alkyl or a C$_6$-C$_{50}$ aryl. In this case, the chromium compound of Formula 3 may be readily prepared by reacting Ph$_2$PCl and R$^5$NH$_2$, which are commercially available at low cost, and thus raw materials are readily available and economical. In particular, when R$^2$ has 18 or more carbon atoms, the solubility of a catalyst in an aliphatic hydrocarbon solvent is high, and thus this compound is suitable for use in industrial processes.

In Formula 2, X, L, A, and Y are the same as described above with regard to the compound of Formula 1. In this case, not only raw materials may be readily available, but manufacturing costs may also be reduced, and thus this compound is more suitable for use in mass-production processes.

A catalyst system according to another embodiment of the present invention includes: the chromium compound of Formula 2 as a main catalyst; and an organic aluminum compound represented by Formula 4 below as a co-catalyst. The catalyst system is very effective for selective conversion of ethylene into 1-hexene and 1-octene. In addition, the catalyst system may realize high activity and high selectivity for 1-hexene and 1-octene without using expensive methylaluminoxane (MAO) obtained by reacting expensive trimethylaluminum with water.

$$(R^3)_3Al \quad \text{[Formula 4]}$$

wherein, in Formula 4, R$^3$ is each independently a C$_1$-C$_{20}$ alkyl group.

In particular, in Formula 4, R$^3$ may be a methyl group, an ethyl group, an n-propyl group, an isopropyl group, an n-butyl group, an isobutyl group, a pentyl group, more particularly, an ethyl group or an isobutyl group.

The biggest advantage of the catalyst system of the present invention is that high activity may be realized using, as a co-catalyst, a compound of Formula 4 wherein $R^3$ is ethyl or isobutyl. The compound of Formula 4 wherein $R^3$ is ethyl or isobutyl is triethylaluminum or triisobutylaluminum, which is mass-produced and used in industry at low cost. Thus, the catalyst system of the present invention may use the compound of Formula 4, which is produced at low cost and raw materials of which are readily available, and realize high activity and high selectivity for 1-hexene and 1-octene, without using expensive methylaluminoxane (MAO).

In particular, in the catalyst system, a molar ratio (Cr:Al) of the chromium compound of Formula 2 and the organic aluminum compound of Formula 4 may range from 1:50 to 1:500. The activity of the catalyst system is further enhanced within the above range.

In one embodiment, the catalyst system may be prepared by separating and purifying the chromium compound of Formula 2, which is a coordination complex formed by reacting the chromium compound of Formula 1 and a bidentate ligand compound, and then reacting the chromium compound of Formula 2 with the organic aluminum compound.

In another embodiment, the catalyst system may be prepared by forming a coordination complex of Formula 2 by reacting the chromium compound of Formula 1 and a bidentate ligand compound, and then adding an organic aluminum compound thereto without separation and purification.

In an embodiment, the catalyst system may further include a hydrocarbon solvent substituted with a halogen or an unsubstituted hydrocarbon solvent. When including such a solvent, the catalyst system may be present in the form of a homogenous solution in which the reaction product is dissolved in a solvent.

More particularly, the hydrocarbon solvent substituted with a halogen or the unsubstituted hydrocarbon solvent may be, for example, toluene, xylene, chlorobenzene, dichlorobenzene, dichloromethane, methylcyclohexane ($MeC_6H_{11}$), cyclohexane ($C_6H_{12}$), cyclohexene ($C_6H_{10}$), or the like. When the listed solvents are used, the catalyst system of the present invention is easily formed, and they are more advantageous for separating 1-hexene and 1-octene, which are reaction products of an oligomerization reaction, from the solvent.

According to another embodiment of the present invention, there is provided a method of preparing an ethylene oligomer, including selectively preparing 1-hexene and 1-octene by bringing the catalyst system into contact with ethylene monomers.

The catalyst system of the present invention may be present in the form of a homogenous solution, being supported in a carrier, or insoluble particles of a carrier, or the like, and thus the method of preparing an ethylene oligomer (an ethylene oligomerization reaction) may be a liquid-phase or slurry-phase reaction.

In addition, in the method of preparing an ethylene oligomer, reaction conditions may vary depending on the state of a catalyst composition used (homogenous or heterogeneous type (supported type)) and a polymerization method (solution polymerization or slurry polymerization). The degree of modification thereof may be easily obtained by one of ordinary skill in the art.

In particular, when the ethylene oligomerization reaction (polymerization) is performed in a liquid- or slurry-phase, a hydrocarbon solvent substituted with a halogen or an unsubstituted hydrocarbon solvent may be used as a medium.

More particularly, as the hydrocarbon solvent, a $C_4$-$C_{20}$ aliphatic hydrocarbon solvent, a $C_6$-$C_{20}$ aromatic hydrocarbon solvent, a mixture thereof, or the like may be used. For example, the hydrocarbon solvent substituted with a halogen or the unsubstituted hydrocarbon solvent may be toluene, xylene, chlorobenzene, dichlorobenzene, dichloromethane, methylcyclohexane ($MeC_6H_{11}$), cyclohexane ($C_6H_{12}$), cyclohexene ($C_6H_{10}$), or the like. When the listed solvents are used, high polymerization activity is obtained and it is easy to separate 1-hexene and 1-octene, which are reaction products of oligomerization, from the solvent.

In the method of preparing an ethylene oligomer, the amount of the catalyst system used is not particularly limited, but since the catalyst system of the present invention may realize high activity, even when a reaction proceeds using a small amount of the catalyst system, a high yield may be obtained.

In one embodiment, when the oligomerization reaction is carried out with solution polymerization, the catalyst system may be added at a molar concentration (based on Cr) of 0.01 mmol/L to 0.2 mmol/L, for example, 0.05 mmol/L to 0.15 mmol/L, and then continuously adding ethylene monomers thereto to allow a reaction to occur therebetween for 30 minutes to 3 hours, thereby preparing 1-hexene and 1-octene. Ethylene may be continuously added at a pressure of 15 bar to 80 bar, particularly 30 bar to 60 bar, for example, 45 bar.

In addition, the oligomerization reaction temperature may range from room temperature (20° C.) to 150° C., for example, 30° C. to 80° C.

In addition, the oligomerization reaction may be performed batchwise, semi-continuously or continuously.

In one embodiment, according to the method of preparing an ethylene oligomer of the present invention, 1-octene and 1-hexene may be prepared by bringing ethylene monomers and the catalyst system into contact with each other in a cyclohexene solvent. In this case, less generation of by-products, high yield, high activity, and excellent selectivity may be realized, and the production of 1-hexene is high, and thus, when applied to industrial processes, an ethylene oligomerization method with enhanced economic efficiency may be provided. In addition, in some embodiments, by using cyclohexene ($C_6H_{10}$) as a solvent instead of a solvent such as methylcyclohexane ($CH_3C_6H_{11}$) or cyclohexane ($C_6H_{12}$), catalytic activity may be enhanced in an ethylene oligomerization reaction using a chromium catalyst system, the production of 1-hexene may be increased, and the production of an oligomer having 10 or more carbon atoms or polyethylene, which is a by-product, may be reduced.

Cyclohexene ($C_6H_{10}$), which is a compound which is mass-produced and used in industry and is available in a great amount at low cost, is generally used as a reactant in the production of a compound such as caprolactam, adipic acid, maleic acid, cyclohexene oxide, or the like, instead of being used as a reactive solvent. There is no example of the cyclohexene ($C_6H_{10}$) solvent being used as a solvent particularly in an olefin polymerization and/or ethylene oligomerization reaction, rather it has the potential of participating in the ethylene oligomerization reaction due to having an olefin (C=C double bond) in the molecule, and thus is generally not suitable for use as a solvent.

As such, the use of cyclohexene ($C_6H_{10}$) has been limited since the solvent was thought to cause a competitive reaction with ethylene, which is a reactant in an ethylene oligomerization reaction. In one embodiment of the present invention, however, the ethylene oligomerization reaction may be performed using cyclohexene ($C_6H_{10}$) as a solvent. In the ethylene oligomerization method, an olefin group (C=C double bond) of cyclohexene ($C_6H_{10}$) does not participate in the reaction unlike in the related art and merely acts as a solvent, thus contributing to increasing catalytic activity and selectivity.

In addition, cyclohexene ($C_6H_{10}$) has a boiling point of about 83° C., which is much different from boiling points (about 63° C. and about 121° C., respectively) of 1-hexene and 1-octene, and thus is more suitable for use in the subsequent separation process, and accordingly, is more suitable for use as a solvent of the ethylene oligomerization reaction.

MODE OF THE INVENTION

Examples

Hereinafter, the configuration and operation of the present invention will be described in further detail with reference to the following examples. However, these examples are provided for illustrative purposes only and are not intended to limit the scope of the present invention.

Preparation Example 1: Preparation of Bidentate Ligand (1)

5 mL of a dichloromethane solution in which 0.505 g (0.994 mmol) of pentatriacontane-18-amine was dissolved was slowly added at 0° C. to 5 mL of a dichloromethane solution in which 0.482 mg (2.19 mmol) of chlorodiphenylphosphine and 1.00 g (9.94 mmol) of triethylamine were dissolved. After stirring at 0° C. for 30 minutes, the temperature was slowly raised to room temperature. After 14 hours of reaction, the solvent was removed under reduced pressure and 10 mL of hexane was added to the resulting solution. An insoluble solid compound was removed by filtering. The solvent was removed in a vacuum under reduced pressure, the residue was dissolved in dichloromethane, and then acetonitrile was slowly diffused to allow recrystallization, thereby obtaining N-(diphenylphosphino)-N-(pentatriacontane-18-yl)-1,1-diphenyl phosphinoamine as a pure bidentate ligand compound (0.593 g, 68%). $^1$H NMR ($C_6D_6$, 400 MHz) 7.452-7.790 (8H, br, ArH), 7.080-7.163 (12H, m, ArH), 3.512-3.635 (1H, m NCH), 2.110-2.115 (2H, m, NCHCH$_2$), 1.179-1.186 (2H, m, NCHCH$_2$), 1.361-1.202 (60H, m, —CH$_2$—), 0.926 (6H, t, $J_{HH}$=6.4 Hz, CH$_2$CH$_3$)

Preparation Example 2: Preparation of Bidentate Ligand (2)

N-(diphenylphosphino)-N-isopropyl-1,1-diphenylphosphinoamine, a synthesis method of which has been reported in the document (J. AM. CHEM. SOC. 2004, 126, 14712-1471) and raw materials of which are readily available, was prepared.

Example 1: Preparation of Chromium Compound of Formula 1A

[CrCl$_2$(CH$_3$CN)$_4$]$^+$[B(C$_6$F$_5$)$_4$]$^-$     [Formula 1A]

An acetonitrile solution in which 2.540 g (2.67 mmol) of [Ag(CH$_3$CN)$_4$]$^+$[B(C$_6$F$_5$)$_4$]$^-$ was dissolved was slowly added at room temperature to 15 mL of an acetonitrile solution in which 1.00 g (2.67 mmol) of CrCl$_3$(THF)$_3$ was dissolved. After stirring at room temperature for 12 hours, a silver chloride (AgCl) product was removed by filtration. The solvent was removed from the filtrate in a vacuum under reduced pressure to obtain a solid-phase residue with a dark green color. The residue was dissolved again in 4 mL of acetonitrile and recrystallized at −30° C., thereby obtaining a dark-green crystalline compound represented by Formula 1A (1.533 g, 60). Anal. Calcd for C$_{32}$H$_{12}$BCrF$_{20}$N$_4$ (965.14 g mol$^{-1}$): C, 39.8, H, 1.25, N, 5.81%. Found: C, 40.4, H, 1.97, N, 8.58%.

Example 2: Preparation of Chromium Compound of Formula 1B

[CrCl$_2$(THF)$_4$]$^+$[B(C$_6$F$_5$)$_4$]$^-$     [Formula 1B]

1.00 g (0.310 mmol) of the [CrCl$_2$(CH$_3$CN)$_4$]$^+$[B(C$_6$F$_5$)$_4$]$^-$ compound prepared according to Example 1 was dissolved in THF, and then the solvent was removed in a vacuum under reduced pressure. This process was repeated three times and acetonitrile was substituted with THF. The resulting compound was dissolved again in 2 mL of THF and recrystallized at −30° C. to obtain a purple crystal suitable for X-ray crystallography. A molecular structure of the obtained single crystal was identified by X-ray crystallography analysis (see FIG. 1). Anal. Calcd for C$_{40}$H$_{32}$BCrF$_{20}$O$_4$ (1090.37 g mol$^{-1}$): C, 44.1, H, 2.96, O, 5.88%. Found: C, 43.8, H, 3.22, O, 7.94%.

Example 3: Preparation of Chromium Compound of Formula 2A

[{(iPr)N(PPh$_2$)$_2$}CrCl$_2$(CH$_3$CN)$_2$]$^+$[B(C$_6$F$_5$)$_4$]$^-$     [Formula 2A]

Figure 2:
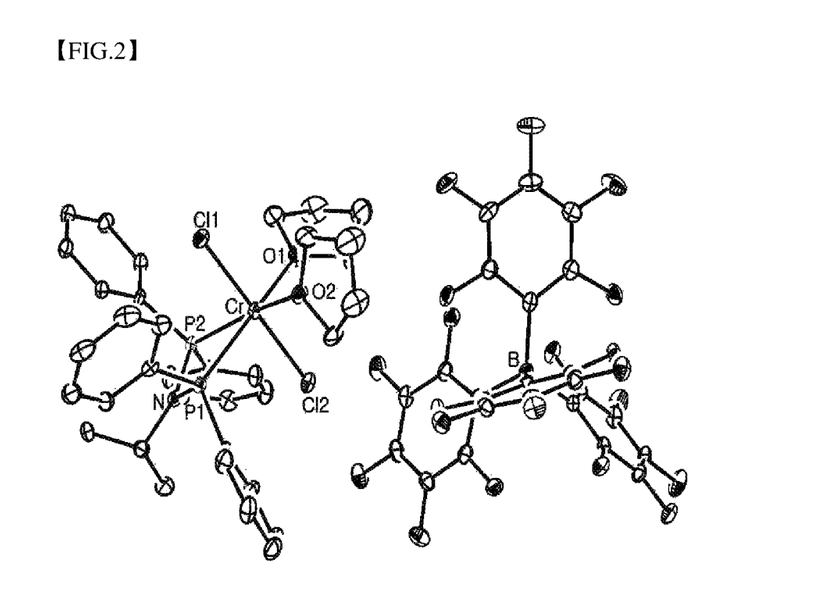
FIG. 2 illustrates a structure of a cationic chromium compound represented by Formula 2A (wherein L∩L is iPrN(PPh$_2$)$_2$, X is chlorine, L is THF, m is 2, A is boron, and Y is $C_6F_5$) that was prepared according to Example 3, wherein the structure was clearly identified by X-ray crystallography.

0.089 g (0.208 mmol) of the N-(diphenylphosphino)-N-isopropyl-1,1-diphenylphosphinoamine compound prepared according to Preparation Example 2 was dissolved in 0.5 mL of dichloromethane, and then slowly added to 1.5 mL of a dichloromethane solution in which 0.200 g (0.207 mmol) of the [CrCl$_2$(CH$_3$CN)$_4$]$^+$[B(C$_6$F$_5$)$_4$]$^-$ compound of Formula 1A prepared according to Example 1 was dissolved. A reaction was allowed to occur therebetween by stirring for 3 hours, and then the solvent was removed in a vacuum under reduced pressure to thereby obtain a blue-green residue. Methylcyclohexane was added to the obtained residue, and then vigorously stirred for 1 to 2 hours to allow trituration. The resulting product was filtered to obtain the compound of Formula 2A as a blue-green powder-type solid phase (0.254 g, 94%). In an 1H NMR spectrum measured after dissolving the obtained compound in CD$_2$Cl$_2$, a signal corresponding to (iPr)N(PPh$_2$)$_2$ was not observed in a normal pattern, from which it was confirmed that the (iPr)N(PPh$_2$)$_2$ ligand coordinated with paramagnetic Cr(III). Anal. Calcd for C$_{55}$H$_{33}$BCl$_2$CrF$_{20}$N$_3$P$_2$ (1311.51 g mol$^{-1}$): C, 50.37, H, 2.54, N, 3.20%. Found: C, 49.49, H, 3.43, N, 2.06%. The resulting compound was dissolved in THF, and then the solvent was immediately removed in a vacuum under reduced pressure, this process was performed again to substitute the coordinated acetonitrile with THF, the obtained compound was dissolved in dichloromethane, followed by diffusion of hexane, thereby obtaining a single crystal. A molecular structure of the obtained single crystal was identified by X-ray crystallography (see FIG. 2).

Example 4: Preparation of Chromium Compound of Formula 2B

[Formula 2B]

0.023 g (0.026 mmol) of the [(CH$_3$)(CH$_2$)$_{16}$]$_2$C(H)N(PPh$_2$)$_2$ compound prepared according to Preparation Example 1 was dissolved in 0.5 mL of dichloromethane, and then slowly added to 0.5 mL of a dichloromethane solution in which 0.050 g (0.052 mmol) of the [CrCl$_2$(CH$_3$CN)$_4$]$^+$[B(C$_6$F$_5$)$_4$]$^-$ of Formula 1A prepared according to Example 1 was dissolved. A reaction was allowed to occur therebetween by stirring for 3 hours, and then the solvent was removed therefrom in a vacuum under reduced pressure to obtain a blue-green residue. The residue was dissolved again in dichloromethane, and then the solvent was removed in a vacuum under reduced pressure to completely remove the remaining acetonitrile. 8 mL of methylcyclohexane was added to the resulting product, and then the temperature was elevated to about 50° C. to dissolve the product, followed by filtration using Celite to thereby remove [CrCl$_2$(CH$_3$CN)$_4$]$^+$[B(C$_6$F$_5$)$_4$]$^-$ which was excessively added and insoluble. The solvent was removed from the filtrate in a vacuum under reduced pressure to obtain a green solid-phase compound (0.032 g, yield: 70). In an $^1$H NMR spectrum measured after dissolving the obtained compound in C$_6$D$_6$, a signal corresponding to [(CH$_3$)(CH$_2$)$_{16}$]$_2$C(H)N(PPh$_2$)$_2$ was not observed in a normal pattern, from which it was confirmed that the ligand coordinated with paramagnetic Cr(III). Anal. Calcd for C$_{87}$H$_{97}$BCl$_2$CrF$_{20}$N$_3$P$_2$ (1760.38 g mol$^{-1}$): C, 59.36, H, 5.55, N, 2.39%. Found: C, 59.69, H, 7.06, N, 1.44%.

Example 5: Preparation of Chromium Compound of Formula 2C

[Formula 2C]

0.5 mL of a dichloromethane solution in which 0.055 mg (0.0660 mmol) of [H(Et$_2$O)$_2$]$^+$[B(C$_6$F$_5$)$_4$]$^-$ was dissolved was added to 0.3 mL of a dichloromethane solution in which 0.030 g (0.066 mmol) of (o-Me$_2$NC$_6$H$_4$CH$_2$)$_3$Cr(III) was dissolved, and then the resulting solution was stirred for 1 hour. The color of the resulting solution changed from red to purple. 0.058 g (0.066 mmol) of the [(CH$_3$)(CH$_2$)$_{16}$]$_2$C(H)N(PPh$_2$)$_2$ ligand prepared according to Preparation Example 1 was dissolved in 5 mL of dichloromethane, and then further added to the reaction solution for 1 hour. A reaction was allowed to occur therebetween by stirring at room temperature for 12 hours, and as a result, the purple color was slowly changed to green. The solvent was removed in a vacuum under reduced pressure, and then the obtained residue was dissolved again in anhydrous dichloromethane, and then the solvent was removed in a vacuum under reduced pressure to completely remove acetonitrile generated as a by-product. 8 mL of methylcyclohexane was added to the resulting product, and then the product was heated to about 50° C. to dissolve the product, followed by fitration using Celite. The solvent was removed from the filtrate in a vacuum under reduced pressure to obtain a green solid-phase compound (0.043 g, yield: 35%). In an 1H NMR spectrum measured after dissolving the obtained compound in C$_6$D$_6$, a signal corresponding to [(CH$_3$)(CH$_2$)$_{16}$]$_2$C(H)N(PPh$_2$)$_2$ was not observed in a normal pattern, from which it was confirmed that the ligand coordinated with paramagnetic Cr(III).

Example 6: Ethylene Oligomerization Reaction Using Catalyst System Consisting of Compound of Formula 2A and Me$_3$Al in Chlorobenzene Solvent 19 mL of chlorobenzene and 10.8 mg (0.150 mmol) of Me$_3$Al were added to an autoclave in a dry box, and then the autoclave was taken out of the dry box to raise the temperature of the autoclave to 60° C. 2.0 mg (0.0015 mmol) of the chromium compound of Formula 2A prepared according to Example 3 was dissolved in 0.5 mL of chlorobenzene, and then 22 mg (0.300 mmol) of Me$_3$Al was added to prepare a catalyst solution such that a total volume of the solution reached 1 mL. A reaction was allowed to occur between the chromium compound and the aluminum compound, Me$_3$Al for 5 minutes to produce an activated catalyst species, and then the activated catalyst species was injected into the autoclave via a syringe and ethylene was injected thereinto at a pressure of 30 bar, followed by polymerization at 75° C. for 30 minutes. The temperature of the reactor was reduced using ice, and then the ethylene gas was removed via an opened valve, and 2 mL of ethanol and 2 mL of a 10% aqueous hydrochloric acid solution were added thereto to terminate the reaction. For gas chromatography analysis, nonane was quantified as a standard (~700 mg) and added, and then some samples were taken and the product was quantitatively analyzed by GC analysis. In addition, the formed polymer was separated through filtration and dried in a vacuum oven, and a mass thereof was measured. The oligomerization results are shown in Tables 1 and 2 below.

Example 7: Ethylene Oligomerization Reaction Using Catalyst System Consisting of Compound of Formula 2A and Et$_3$Al in Chlorobenzene Solvent A procedure was carried out in the same manner as in Example 6 and under the same conditions as those of Example 6, except that Et$_3$Al was used instead of Me$_3$Al and the catalyst activation (reaction between the compound of Formula 2A and Et$_3$Al) time was increased to 1 hour.

Example 8

Ethylene Oligomerization Reaction Using Catalyst System Consisting of Compound of Formula 2A and (iBu)$_3$Al in Chlorobenzene Solvent A procedure was carried out in the same manner as in Example 6 and under the same conditions as those of Example 6, except that (iBu)$_3$Al was used instead of Me$_3$Al and the catalyst activation (reaction between the compound of Formula 2A and (iBu)$_3$Al) time was increased to 1 hour.

Example 9

Ethylene Oligomerization Reaction Using Catalyst System Consisting of Compound of Formula 2B and Me$_3$Al in Chlorobenzene Solvent A procedure was carried out in the same manner as in Example 6 and under the same conditions as those of Example 6, except that the chromium compound of Formula 2B was used instead of the chromium compound of Formula 2A.

Example 10

Ethylene Oligomerization Reaction Using Catalyst System Consisting of Compound of Formula 2B and (iBu)$_3$Al in Methylcyclohexane 19 mL of methylcyclohexane and 20 mg (0.100 mmol) of iBu$_3$Al were added to an autoclave in a dry box, and then the autoclave was taken out of the dry box to raise the temperature of the autoclave to 40° C. 2.6 mg (0.0015 mmol) of the chromium compound of Formula 2B prepared according to Example 4 was dispersed in 1 mL of methylcyclohexane, the dispersion was injected into the autoclave using a syringe, and ethylene was injected thereinto at a pressure of 30 bar to allow polymerization at 45° C. for 30 minutes. Reaction termination and product analysis were performed using the same method as that used in Example 6.

Example 11: Ethylene Oligomerization Reaction Using Catalyst System Consisting of Compound of Formula 2B and Et$_3$Al in Methylcyclohexane A procedure was carried out in the same manner as in Example 10 and under the same conditions as those of Example 10, except that Et$_3$Al was used instead of (iBu)$_3$Al.

Example 12: Ethylene Oligomerization Reaction Using Catalyst System Consisting of Compound of Formula 2B and (Octyl)$_3$Al in Methylcyclohexane A procedure was carried out in the same manner as in Example 10 and under the same conditions as those of Example 10, except that (Octyl)$_3$A was used instead of (iBu)$_3$Al.

Example 13: Ethylene Oligomerization Reaction Using Catalyst System Consisting of Compound of Formula 2C and (iBu)$_3$Al in Methylcyclohexane A procedure was carried out in the same manner as in Example 10 and under the same conditions as those of Example 10, except that the compound of Formula 2C was used instead of the compound of Formula 2B.

Example 14

Ethylene Oligomerization Reaction Using Catalyst System Consisting of Compound of Formula 2B and (iBu)$_3$Al in Methylcyclohexane A procedure was carried out in the same manner as in Example 10 and under the same conditions as those of Example 10, except that the amount of (iBu)$_3$Al was increased from 0.10 mmol to 0.45 mmol, the pressure of ethylene was increased from 30 bar to 45 bar, and the reaction temperature was reduced from 45° C. to 35° C.

Example 15

Ethylene Oligomerization Reaction Using Catalyst System Consisting of Compound of Formula 2B and Et$_3$Al in Cyclohexene (C$_6$H$_{10}$) (1)

In particular, 19 mL of cyclohexene (C$_6$H$_{10}$) and 170 mg (0.450 mmol) of Et$_3$Al were added to an autoclave in a dry box, and then the autoclave was taken out of the dry box to raise the temperature of the autoclave to 35° C. The [{[(CH$_3$)(CH$_2$)$_{16}$]$_2$C(H)N(PPh$_2$)$_2$}CrCl$_2$(NCCH$_3$)$_2$]$^+$[B(C$_6$F$_5$)$_4$]$^-$ compound prepared according to Example 4 was dispersed in 1 mL of cyclohexene (C$_6$H$_{10}$), the dispersion was injected into the autoclave using a syringe, and ethylene was injected thereinto at a pressure of 45 bar to allow polymerization at 45° C. for 30 minutes. Reaction termination and production analysis were performed using the same method as that used in Example 1. The temperature of the reactor was reduced using ice, and then the ethylene gas was removed via an opened valve, and 2 mL of ethanol and 2 mL of a 10% aqueous hydrochloric acid solution were added thereto to terminate the reaction. For gas chromatography analysis, nonane was quantified as a standard (~700 mg) and added, and then some samples were taken and the product was quantitatively analyzed by GC analysis. In addition, the formed polymer was separated through filtration and dried in a vacuum oven, and mass thereof was measured.

Example 16: Ethylene Oligomerization Reaction Using Catalyst System Consisting of Compound of Formula 2B and Et$_3$Al in Cyclohexene (C$_6$H$_{10}$) (2)

In particular, a procedure was carried out in the same manner as in Example 15, except that the reaction time was increased to 1 hour.

Example 17: Ethylene Oligomerization Reaction Using Catalyst System Consisting of Compound of Formula 2B and (iBu)$_3$Al in Cyclohexene (C$_6$H$_{10}$)

In particular, a procedure was carried out in the same manner as in Example 15, except that (iBu)$_3$Al was used instead of Et$_3$Al.

Comparative Example 1: Ethylene Oligomerization Reaction Using MAO in Chlorobenzene 19 mL of chlorobenzene and 170 mg (0.450 mmol) of MAO (modified-MAO, manufactured by Akzo-Nobel, 7 wt %-Al) were added to an autoclave in a dry box, and then the autoclave was taken out of the dry box to raise the temperature of the autoclave to 60° C. 2.0 mg (0.0015 mmol) of (iPrN(PPh$_2$)$_2$)CrCl$_3$ was dissolved in 1 mL of chlorobenzene, the resulting solution was injected into the autoclave using a syringe, and ethylene was injected thereinto at a pressure of 30 bar to allow polymerization at 75° C. for 30 minutes. Reaction termination and product analysis were performed in the same manner as in Example 1.

Comparative Example 2: Ethylene Oligomerization Reaction Using MAO in Methylcyclohexane A procedure was carried out in the same manner as in Comparative Example 1 and under the same conditions as those in Comparative Example 1, except that methylcyclohexane was used as a reactive solvent instead of chlorobenzene.

Comparative Example 3: Ethylene Oligomerization Reaction Using MAO in Methylcyclohexane A procedure was carried out in the same manner as in Comparative Example 1 and under the same conditions as those in Comparative Example 1, except that methylcyclohexane was used as a reactive solvent instead of chlorobenzene, and a mixture of 0.0015 mmol of iPrN(PPh$_2$)$_2$ and 0.0015 mmol of Cr(acac)$_3$ was added into the autoclave instead of (iPrN(PPh$_2$)$_2$)CrCl$_3$.

The types of the solvents, the chromium compounds, and the organic aluminum compounds used in Examples 6 to 17 and Comparative Examples 1 to 4 are shown in Table 1 below.

TABLE 1

| | Solvent | Cr-compound | Cr-compound concentration (mmol) | Al-compound | Al-compound concentration (mmol) |
|---|---|---|---|---|---|
| Example 6 | $C_6H_5Cl$ | Formula 2A | 0.0015 | $Me_3Al$ | 0.300 |
| Example 7 | $C_6H_5Cl$ | Formula 2A | 0.0015 | $Et_3Al$ | 0.300 |
| Example 8 | $C_6H_5Cl$ | Formula 2A | 0.0015 | $(iBu)_3Al$ | 0.300 |
| Example 9 | $C_6H_5Cl$ | Formula 2B | 0.0015 | $Me_3Al$ | 0.300 |
| Example 10 | $MeC_6H_{11}$ | Formula 2B | 0.0015 | $(iBu)_3Al$ | 0.100 |
| Example 11 | $MeC_6H_{11}$ | Formula 2B | 0.0015 | $Et_3Al$ | 0.100 |
| Example 12 | $MeC_6H_{11}$ | Formula 2B | 0.0015 | $(Octyl)_3Al$ | 0.100 |
| Example 13 | $MeC_6H_{11}$ | Formula 2C | 0.0015 | $(iBu)_3Al$ | 0.100 |
| Example 14 | $MeC_6H_{11}$ | Formula 2B | 0.0015 | $(iBu)_3Al$ | 0.450 |
| Example 15 (0.5 h) | $C_6H_{10}$ | Formula 2B | 0.0015 | $Et_3Al$ | 0.450 |
| Example 16 (1 h) | $C_6H_{10}$ | Formula 2B | 0.0015 | $Et_3Al$ | 0.450 |
| Example 17 | $C_6H_{10}$ | Formula 2B | 0.0015 | $(iBu)_3Al$ | 0.450 |
| Comparative Example 1 | $C_6H_5Cl$ | $(iPrN(PPh_2)_2)CrCl_3$ | 0.0015 | MMAO | 0.450 |
| Comparative Example 2 | $MeC_6H_{11}$ | $(iPrN(PPh_2)_2)CrCl_3$ | 0.0015 | MMAO | 0.450 |
| Comparative Example 3 | $MeC_6H_{11}$ | $iPrN(PPh_2)_2$ + $Cr(acac)_3$ | 0.0015 | MMAO | 0.450 |
| Comparative Example 4 (Reference)[c] | $MeC_6H_5$ | $(iPrN(PPh_2)_2)CrCl_3$ + $[Ph_3C]^+[B(C_6F_5)_4]^-$ | — | $(iBu)_3Al$ | — |

The activity of each of the olefin polymerization reactions in Examples 6 to 17 and Comparative Examples 1 to 4 and the composition of each of the prepared polymers thereof are shown in Table 2 below.

TABLE 2

| | Activity[a] | $C_1$-$C_6$ (%) | Cy-$C_6$[b] (%) | $C_1$-$C_8$ (%) | >$C_{10}$ (%) | Other (%) | PE (%) |
|---|---|---|---|---|---|---|---|
| Example 6 | 155 | 41.6 | 2.4 | 43.7 | 9.4 | 0.7 | 2.2 |
| Example 7 | 224 | 44.3 | 2.3 | 40.6 | 11.4 | 0.1 | 1.3 |
| Example 8 | 221 | 37.5 | 2.1 | 46.6 | 12.6 | 0.2 | 1.0 |
| Example 9 | 140 | 50.2 | 2.1 | 37.3 | 8.7 | 0.1 | 1.6 |
| Example 10 | 76 | 18.7 | 5.1 | 68.6 | 5.1 | 0.3 | 2.2 |
| Example 11 | 58 | 18.3 | 5.1 | 69.7 | 6.1 | 0.7 | 0.1 |
| Example 12 | 66 | 16.4 | 5.6 | 68.7 | 7.9 | 0.8 | 0.6 |
| Example 13 | 81 | 24.3 | 4.2 | 61.9 | 5.8 | 0.7 | 3.1 |
| Example 14 | 159 | 9.4 | 5.3 | 73.2 | 9.8 | 0.8 | 1.5 |
| Example 15 | 168 | 14.2 | 4.9 | 71.7 | 7.5 | 1.6 | 0.1 |
| Example 16 | 160 | 14.2 | 4.9 | 74.6 | 8.0 | 1.0 | 0.3 |
| Example 17 | 168 | 15.2 | 4.9 | 74.1 | 5.3 | 0.2 | 0.3 |
| Comparative Example 1 | 203 | 44.9 | 2.2 | 39.6 | 11.3 | 0.8 | 1.2 |
| Comparative Example 2 | 234 | 29.1 | 3.2 | 51.4 | 12.7 | 0.1 | 3.5 |
| Comparative Example 3 | 122 | 21.7 | 3.5 | 58.9 | 8.5 | 0.7 | 6.7 |
| Comparative Example 4 (Reference)[c] | 11 | 5.3 | 2.7 | 38.5 | 7.9 | 0.5 | 45.1 |

[a] unit: Kg (total amount of product)/g (catalyst (Cr))/hr.
[b] methylcyclopentane + methylenecyclopentane.
[c] Organometallics 2007, 26, 1108.

From the results of Table 2, it was confirmed that olefin polymerization of Examples 6 to 17 using the chromium compound of Formula 2 and not using expensive MAO used an organic aluminum compound in a reduced amount, and realized high activity similar to that of the cases of Comparative Examples 1 to 3 including a large amount of expensive MAO, high selectivity for 1-hexene and 1-octene, and an effect of reducing polyethylene, which is a by-product.

In particular, it was confirmed that the cases of Examples 15 to 17, in which 1-octene and 1-hexene were prepared by bringing ethylene monomers and a chromium catalyst system into contact with each other in a cyclohexene solvent, exhibited high catalytic activity, produced less of a component with 10 or more carbon atoms as a by-product and PE, and exhibited increased amounts of produced 1-hexene and 1-octene.

In contrast, the cases of Comparative Examples 1 to 3 had to include a large amount of expensive MAO to realize high activity similar to that of the examples of the present invention, high selectivity for 1-hexene and 1-octene, and an effect of reducing polyethylene, which is a by-product.

In addition, although the case of Comparative Example 4 is a bis(phosphine)/$CrCl_3$/$[Ph_3C]^+[B(C_6F_5)_4]^-$ (1 eq)/$Et_3Al$ (or $iBu_3Al$) catalyst system which mimics a metallocene-based polyolefin catalyst system reported in the cited reference (Organometallics 2007, 26, 1108), it failed to realize high activity and also produced a large amount of polyethylene as a by-product.

Simple changes or modifications may be carried out by those of ordinary skill in the art without undue difficulty, and these changes or modifications should be construed as being within the scope of the present invention.

The invention claimed is:

1. A chromium compound of Formula 2 below:

[(L∩L)$CrX_2L_m$]$^+$[$AY_4$]$^-$         Formula 2 wherein, in Formula 2,
(L∩L) is a bidentate chelating ligand of the following formula 3:

($R^1$)$_2$P—Z—P($R^1$)$_2$         Formula 3 wherein, in Formula 3,
  $R^1$ is each independently a $C_1$-$C_{50}$ alkyl group or a $C_6$-$C_{50}$ aryl group; and
  Z is a $C_2$-$C_{50}$ alkylene group, a $C_6$-$C_{50}$ arylene group, or —N($R^2$)— that links the two P atoms, wherein $R^2$ is a $C_1$-$C_{50}$ alkyl or a $C_6$-$C_{50}$ aryl;
X is each independently a halogen, a $C_2$-$C_{30}$ carboxylate, acetylacetonate, or a $C_1$-$C_{30}$ hydrocarbyl having or not having at least one of an ether group and an amine group;

L is each independently a $C_2$-$C_{30}$ nitrile, a $C_2$-$C_{30}$ ether, or a $H_2O$ ligand;
m is an integer of 0 to 2;
A is boron; and
Y is a $C_6$-$C_{20}$ fluorine-substituted aryl, a $C_6$-$C_{20}$ fluorine-substituted aryloxy, or a $C_1$-$C_{20}$ fluorine-substituted alkoxy.

2. The chromium compound of claim 1, wherein, in Formula 3, $R^1$ is phenyl, and Z is —$N(R^2)$— wherein $R^2$ is a $C_1$-$C_{50}$ alkyl or a $C_6$-$C_{50}$ aryl.

3. An ethylene oligomerization catalyst system comprising:
a chromium compound of Formula 2 below; and
an organic aluminum compound of Formula 4 below:

$$[(L\cap L)CrX_2L_m]^+[AY_4]^- \qquad \text{Formula 2}$$

wherein, in Formula 2,
($L\cap L$) is a bidentate chelating ligand of the following Formula 3:

$$(R^1)_2P{-}Z{-}P(R^1)_2 \qquad \text{Formula 3}$$

wherein, in Formula 3,
$R^1$ is each independently a $C_1$-$C_{50}$ alkyl group or a $C_6$-$C_{50}$ aryl group; and
Z is a $C_2$-$C_{50}$ alkylene group, a $C_6$-$C_{50}$ arylene group, or —$N(R^2)$— that links the two P atoms, wherein $R^2$ is a $C_1$-$C_{50}$ alkyl or a $C_6$-$C_{50}$ aryl;
X is each independently a halogen, a $C_2$-$C_{30}$ carboxylate, acetylacetonate, or a $C_1$-$C_{30}$ hydrocarbyl having or not having at least one of an ether group and an amine group;
L is each independently a $C_2$-$C_{30}$ nitrile, a $C_2$-$C_{30}$ ether, or a $H_2O$ ligand;
m is an integer of 0 to 2;
A is boron; and
Y is a $C_6$-$C_{20}$ fluorine-substituted aryl, a $C_6$-$C_{20}$ fluorine-substituted aryloxy, or a $C_1$-$C_{20}$ fluorine-substituted alkoxy, $$(R^3)_3Al \qquad \text{Formula 4}$$

wherein, in Formula 4, $R^3$ is a $C_1$-$C_{20}$ alkyl group.

4. The ethylene oligomerization catalyst system of claim 3, wherein, in Formula 4, $R^3$ is ethyl or isobutyl.

5. The ethylene oligomerization catalyst system of claim 3, wherein a molar ratio of the chromium compound of Formula 2 and the organic aluminum compound of Formula 4 ranges from 1:50 to 1:500.

6. A method of selectively preparing 1-hexene and 1-octene, comprising contacting ethylene monomers with a catalyst system,
said catalyst system comprising:
(a) a chromium compound of Formula 2 below; and
(b) an organic aluminum compound of Formula 4 below:

$$[(L\cap L)CrX_2L_m]^+[AY_4]^- \qquad \text{Formula 2}$$

wherein, in Formula 2,
($L\cap L$) is a bidentate chelating ligand of the following Formula 3:

$$(R^1)_2P{-}Z{-}P(R^1)_2 \qquad \text{Formula 3}$$

wherein, in Formula 3,
$R^1$ is each independently a $C_1$-$C_{50}$ alkyl group or a $C_6$-$C_{50}$ aryl group; and
Z is a $C_2$-$C_{50}$ alkylene group, a $C_6$-$C_{50}$ arylene group, or —$N(R^2)$— that links the two P atoms, wherein $R^2$ is a $C_1$-$C_{50}$ alkyl or a $C_6$-$C_{50}$ aryl;
X is each independently a halogen, a $C_2$-$C_{30}$ carboxylate, acetylacetonate, or a $C_1$-$C_{30}$ hydrocarbyl having or not having at least one of an ether group and an amine group;
L is each independently a $C_2$-$C_{30}$ nitrile, a $C_2$-$C_{30}$ ether, or a $H_2O$ ligand;
m is an integer of 0 to 2;
A is boron; and
Y is a $C_6$-$C_{20}$ fluorine-substituted aryl, a $C_6$-$C_{20}$ fluorine-substituted aryloxy, or a $C_1$-$C_{20}$ fluorine-substituted alkoxy, $$(R^3)_3Al \qquad \text{Formula 4}$$

wherein, in Formula 4, $R^3$ is a $C_1$-$C_{20}$ alkyl group.

7. The method of claim 6, wherein the contacting of the catalyst system and the ethylene monomers is carried out in a cyclohexene solvent.

8. The method of claim 6, wherein, in Formula 4, $R^3$ is ethyl or isobutyl.

9. The method of claim 8, wherein the contacting of the catalyst system and the ethylene monomers is carried out in a cyclohexene solvent.

10. The method of claim 6, wherein, a molar ratio of the chromium compound of Formula 2 and the organic aluminum compound of Formula 4 ranges from 1:50 to 1:500.

11. The method of claim 10, wherein the contacting of the catalyst system and the ethylene monomers is carried out in a cyclohexene solvent.

* * * * *